United States Patent [19]

Robertson et al.

[11] Patent Number: 5,004,864
[45] Date of Patent: Apr. 2, 1991

[54] DOMINANT AMYLOSE-EXTENDER MUTANT OF MAIZE

[75] Inventors: Donald S. Robertson; Philip S. Stinard, both of Ames, Iowa

[73] Assignee: Iowa State University Research Foundation, Inc., Ames, Iowa

[21] Appl. No.: 276,882

[22] Filed: Nov. 28, 1988

[51] Int. Cl.$^5$ .................. A01H 5/00; C12N 15/00
[52] U.S. Cl. .................... 800/235; 800/230; 435/172.1; 435/172.3; 935/6; 935/66
[58] Field of Search .................. 47/58, DIG. 1; 435/172.1, 172.3; 536/27; 800/230, 235

[56] References Cited

PUBLICATIONS

Freeling (1984), Ann Rev. Plant Physiology 35:277–298.
Stinard et al, (1987) Maize Genetics Coop. News Letter #61, pp. 7–8.
Sprague et al, (1977) Jn. Corn & Corn Improvement, Ed. Sprague, p. 316, Amer. Soc. Agron., Madison Wiscon.

*Primary Examiner*—Charles F. Warren
*Assistant Examiner*—Gary Benzion
*Attorney, Agent, or Firm*—Tilton, Fallon, Lungmus, & Chestnut

[57] ABSTRACT

A transferrable maize gene is disclosed which is a dominant mutant allele at the amylose-extender (ae) locus. Maize seeds having this gene produce a high-amylose starch.

11 Claims, No Drawings

DOMINANT AMYLOSE-EXTENDER MUTANT OF MAIZE

GRANT REFERENCE

This invention was made with government support under DCB 8608188 awarded by National Science Foundation. The Government has certain rights in the invention.

FIELD OF INVENTION

This invention relates to mutants of maize which produce high-amylose starch, which are called *amylose-extender* or *ae* mutants.

BACKGROUND OF INVENTION

Maize starch is composed of two glucose polymers: (1) amylose which is a straight chain molecule, and (2) amylopectin which is a branched chain molecule. Mutations at the *amylose-extender*, or ae, locus of maize result in an increase in the amylose content of the endosperm relative to its amylopectin content. For example, the increase may be from around 25% to as high as 70% (Shannon, J. C. and Garwood, D. L., 1984, Genetics and Physiology of Starch Development in *Starch: Chemistry and Technology*, 2nd edition, ed. E. F. Faschall, Academic Press, Inc. Orlando, pp. 25-86). Starch with high amylose content can be used to produce tough, edible or biodegradable films and gels (*Starch: Chemistry and Technology*, 2nd edition, ed E. F. Faschall, Academic Press, Inc., Orlando, 1984).

To date, all reported ae mutants have been simple recessives, requiring the mutants to be homozygous in order to produce starch with sufficiently high amylose content. (Zuber, M. S., Grogan, C. O., Deatherage, W. L., Hubbard, J. E., Schulze, W. E. and MacMasters, M. M., 1958. Breeding high amylose corn. *Agronomy Journal* 50:9-12. Vineyard, M. L., Bear, R. P., MacMasters, M. M. and Deatherage, W. L., 1958. Development of "Amylomaize"--corn hybrids with high amylose starch: I. Genetic considerations. *Agronomy Journal* 50:595-598. Helm, J. L., Fergason, V. L. and Zuber, M. S., 1967. Development of high-amylose corn (*Zea mays* L.) by the backcross method. *Crop Science* 7:659-662. Garwood, D. L., Shannon, J. C. and Creech, R. G., 1976. Starches of endosperms processing different alleles at the *amylose-extender* locus of *Zea mays* L. *Cereal Chemistry* 53:355-364.) The known recessive mutant alleles of the *amylose-extender* locus have already proven useful in the production of high-amylose starches. The amylose content of starches from the best recessive ae hybrids currently available is around 70%. (Shannon, J. C. and Garwood, D. L., 1984. Genetics and Physiology of Starch Development in *Starch: Chemistry and Technology*. 2nd edition ed. E. F. Faschall, Academic Press Inc. Orlando. pp. 25-86.) Current techniques require the development of homozygous ae inbreds, followed by the production of hybrid seed for planting in open-pollinated production fields.

A dominant mutant allele at the ae locus, if available, could be used to accelerate the development of high-amylose inbred or hybrid lines because such a dominant genetic trait, which produces the high-amylose starch, expresses itself in every generation of crossing and thus is readily followed. The recessive ae mutant alleles are not as readily followed in a crossing regime. A dominant mutant allele can be expected to have other uses and advantages.

SUMMARY OF INVENTION

We have isolated from our Mutator transposable element stock an ae mutant allele, Ae-5180, that is dominant, requiring the presence of only one dose of Ae-5180 in the endosperm to produce a kernel with the glassy-sugary phenotype characteristic of homozygous ae. It has been found that homozygous lines of Ae-5180, developed without selection for high amylose, can produce starch with an amylose content as high as 72%. Lines with one or two Ae-5180 alleles in the endosperm also have amylose contents of 70%. Therefore, this mutant is uniquely adaptable for breeding purposes because the triploid endosperm of maize produces the same high level of amylose whether Ae-5180 is present in one, two, or three copies. It is expected that selection of Ae-5180 lines for a higher amylose content could increase the perdent amylose.

In addition to providing an improved means for production of high-amylose starch varieties of hybrid maize for users of high-amylose starch, it is expected that the dominant ae mutant of this invention will have other uses. Recessive ae alleles are known to alter the branching and chain length of kernel starches. They also interact in unique ways with other mutants that alter the structure of maize starches, such as waxy, dull, and sugary (Vineyard, M. L., Bear, R. P., MacMasters, M. M., and Deatherage, W. L., 1958. Development of "Amylomaize"--Corn hybrids with high amylose starch: I. Genetic considerations. *Agronomy Journal* 50:595-598. Kramer, H. H., Whistler, R. I., and Anderson, E. G., 1956. A new gene interaction in the endosperm of maize. *Agronomy Journal* 48:170-172.) It may be possible to cross Ae-5180 into other mutant lines to tailor-make starches to suit special industrial uses. Hybrids between Ae-5180 and currently existing recessive ae inbreds may result in synergistic effects between the dominant and recessive alleles that could result in an increased amylose content of kernel starch, or result in alternations in starch quality which may have commercial value. Ae-5180 could be used to accelerate the development of high-amylose inbred and hybrid lines.

When Ae-5180 is crossed as a male to an inbred line, the $F_1$ kernels express a mutant phenotype that is characteristic for a given inbred. If the amylose content of the $F_1$ kernels is predictive of the amylose content of Ae-5180 after it has been converted to the inbred background, then promising high-amylose inbreds could be selected for further development after one generation of crosses. Likewise, it may be possible to select promising high-amylose hybrids by crossing Ae-5180 to different elite hybrids and analyzing the amylose content of the progeny kernels. Ae-5180 may allow the use of novel techniques for the production of high-amylose maize.

Current techniques using recessive mutant alleles require the development of homozygous ae inbreds, followed by the production of hybrid seed for planting in open-pollinated fields. High-amylose Ae-5180 material could also be produced in this manner. Alternatively, because Ae-5180 induces high amylose levels (70%) when in one or two copies in the endosperm, one could adapt systems of detasseling or cytoplasmic male sterility to produce female rows of wildtype starchy hybrids that could be pollinated by homozygous Ae-5180 male rows. This system could be used to take advantage of currently available elite starchy hybrid lines and thereby tremendously increase the yield of high-amylose kernels.

DETAILED DISCLOSURE

In our 1984 yl wx gl8/Yl Wx Gl8 Mu isolation plot, a single glassy kernel was observed in a population of 388,688 kernels. We planted this kernel in 1985, and self-pollinated and outcrossed the resulting plant to a standard starchy line (Standard Q60). The self-pollinated ear segregated for a sugary kernel type in an approximate 1:2 ratio of starchy to sugary kernels. The outcross ear segregated in an approximate 2:1 ratio of starchy to sugary kernels. Thus, it appeared that our mutant (which we first designated Su*-5180) was dominant, but was transmitted in a reduced frequency since the ratios observed differ significantly ($p<0.001$) from the expected values of 1:3 and 1:1 in the self and outcross respectively (Table 1).

TABLE 1

Counts of starchy and sugary kernels on the self and outcross ears of the original Ae-5180 mutant plant grown in 1985. The outcross was made to a standard starchy line.

| Plant No. | Selfed ear | | | Male Outcross ear | | |
|---|---|---|---|---|---|---|
|  | Starchy | Sugary | % Sugary | Starchy | Sugary | % Sugary |
| 5180-1 | 123 | 244 | 66.5 | 213 | 103 | 32.4 |
|  | 1:3 Chi-square = 14.1916 | | | 1:1 Chi-square = 39.4465 | | |
|  | ($p<0.001$) | | | ($p<0.001$) | | |

Further tests (described below) showed that Su*-5180 is fully female transmissible, but frequently shows reduced transmission through the male, when in competition with wildtype pollen, as is the situation in a heterozygous plant. We tested Su*-5180 for allelism with su1, su2, du and ae, because these mutants have a sugary or glassy phenotype similar to that of Su*5180. Selfs of (Su*-5180/su1), (Su*-5180/su2), and (Su*-5180/du) segregated for fully starchy kernels as well as the parental types and their presumed combinations (double mutants). Such results are expected if Su*-5180 is not allelic to su1, su2, or du. The selfs of (Su*-5180/ae), however, produced only sugary or glassy kernels, a result expected if Su*-5180 is a dominant mutant allele of ae. Backcrosses of (Su*-5180/ae) by ae ae stocks also produced ears with only sugary or glassy kernels, confirming the allelism of Su*-5180 with ae. We now designate our dominant *amylose-extender* mutant Ae-5180.

The expression of Ae-5180 in our standard backgrounds varies from slightly shrunken and tarnished to wrinkled sugary to brittle. This variability occurs whether Ae-5180 is present in the endosperm in 1, 2, or 3 doses. We have made F1 reciprocal crosses of Ae-5180 to several different inbred lines, and observed that the phenotype of the F1 kernels seems to show a maternal effect. When our standard lines carrying Ae-5180 are used as the female parent in the inbred crosses, the F1 kernels exhibit the variability in phenotype noted above. However, when the inbred lines are used as females, the expression of Ae-5180 is consistent for a given inbred, but varies depending on which inbred is the female parent. The inbred B73 shows the most extreme expression, the mutant kernels having a glassy, near-brittle appearance. The inbreds Mo17, Oh43, N25, and A636 show good expression, with mutant kernels that are sugary and slightly wrinkled. The inbreds M14, W22, B37, A632, B76, and H99 show fair expression, with smooth, slightly translucent mutant kernels. Mutant kernels can barely be distinguished in crosses to Tama Flint, having a weakly translucent, frosted appearance. We anticipate that after Ae-5180 has been backcrossed into these inbreds for several generations, the above phenotypes will be consistently expressed.

In order to further characterize Ae-5180, and to generate potentially useful stocks, we conducted linkage tests of Ae-5180 with a series of waxy translocations, and the chromosome 5 linkage markers gl8 and a2. The three T5-9 waxy translocations that we selected all showed linkage with Ae-5180 (Table 2).

TABLE 2

Linkage data for Ae-5180 to waxy marked translocations (wxT). Testcross: (Ae-5180 Wx / Ae wxT) × wx wx

| wxT | Ae-5180 wx | Ae wx | Ae-5180 wx | Ae Wx | % Recomb. |
|---|---|---|---|---|---|
| 5-9c | 335 | 288 | 29 | 67 | 13.4 ± 1.3 |
| 5-9 (4790) | 391 | 325 | 84 | 131 | 23.1 ± 1.4 |
| 5-9a | 354 | 324 | 179 | 165 | 33.7 ± 1.5 |

| Breakpoints: | 5-9c | 5S.07 9L.10 |
|---|---|---|
|  | 5-9 (4790) | 5L.34 9L.45 |
|  | 5-9a | 5L.69 9S.17 |

The tightest linkage to wx ($p=13.4$ cM) was with T5-9c, which has a breakpoint in the short arm of chromosome 5 close to the centromere. This is not surprising, since ae is on the long arm of chromosome 5, about 15 cM from the centromere. We might have expected even closer linkage of Ae-5180 with wx T5-9 (4790), which has a breakpoint at 5L.34, especially since ae had been previously shown by J. N. Jenkins (Ph.D. thesis, Purdue, 1960) to be very close to the T4-5c breakpoint at 5L.27. Instead we found linkage of $p=23.1$ cM. Such a high percent recombination with waxy could be at least partially explained by the chromosome 9 breakpoint of wx T5-9 (4790), 9L.45, being at least 10 cM, and perhaps as many as 26 cM, from the waxy locus on the chromosome 9 linkage map. Crossovers occurring in the region between wx and the chromosome 9 breakpoint would increase the apparent linkage distance between ae and wx in this particular translocation. It is frequently difficult to correlate linkage maps with cytological maps with any degree of precision. The important point to note is that Ae-5180 does indeed show linkage with translocations involving chromosome 5. One other point of interest is that the parental and crossover classes in the wx translocation linkage data are not well-balanced. There seems to be about an equal number of plump (Ae) and sugary (Ae-5180) kernels in each set of translocation data, but for each translocation there seems to be an excess of Wx kernels.

Our linkage data for Ae-5180 and gl8 (12.5±0.8 cM, Table 3) are in close agreement with the value of 11 cM reported on the 1988 linkage map for recessive ae (Maize Genetics Cooperation Newsletter, 62:142, 1988). There appears to be an abundance of starchy (Ae) kernels over sugary (Ae-5180) kernels, but this is due to the lower percent germination of the sugary kernels when we were seedling-testing for gl8. The linkage data for a2 and Ae-5180 (Table 4) yield a value (13.1+0.7 cM) that is somewhat less than the reported value for a2 to ae of 22 cM, but is in agreement with a two-point test made by Jenkins, who found a value of 14 cM for a2 to ae in a backcross test.

TABLE 3

Linkage data for Ae-5180 to gl8.
Testcross: (Ae-5180 G18 / Ae gl8) × Ae Ae gl8 gl8

| Reg | Genotype | | No. | Totals |
|---|---|---|---|---|
| 0 | Ae-5180 | + | 700 | |
|   | +       | gl8 | 973 | 1673 |
| 1 | Ae-5180 | gl8 | 103 | |
|   | +       | +   | 136 | 239 |

% Recombination Ae-5180 − gl8 = 12.5 ± 0.8

TABLE 4

Linkage data for a2 to Ae-5180
Testcross: a2 a2 Ae Ae × (a2 Ae-5180/A2 Ae)

| Reg | Genotype | | No. | Totals |
|---|---|---|---|---|
| 0 | a2 | Ae-5180 | 899 | |
|   | +  | +       | 1028 | 1927 |
| 1 | a2 | +       | 155 | |
|   | +  | Ae-5180 | 135 | 290 |

% Recombination a2 − Ae-5180 = 13.1 ± 0.7

We have crossed Ae-5180 into homozygous wx stocks in order to observe whether Ae-5180 shows the same phenotypic interaction with waxy as does the standard ae allele. Kernels that are homozygous for the standard ae allele and homozygous for wx are smaller, more translucent, and have finer wrinkling than kernels that are homozygous for ae in a Wx background. The latter kernels are translucent and slightly wrinkled, but not as extremely so as those in a wx background. This effect is very striking, and requires the ae allele to be homozygous (ae ae ae) in the endosperm. If only one or two doses of ae are present, the kernels will be full and plump in either a wx or Wx background (It has been reported that in certain wx lines, it is possible to distinguish a dosage effect for ae, but we have not observed this in our lines.) Ae-5180, on the other hand, can produce the same effect in only one dose, Ae-5180 Ae Ae wx wx wx kernels (where Ae represents the wildtype starchy allele of *amylose-extender*) are uniformly small, translucent, and finely wrinkled. Ae-5180 Ae Ae Wx Wx Wx kernels, on the other hand, are usually just slightly smaller in size than wildtype starchy kernels, and show the wider phenotypic range from slightly translucent to wrinkled-sugary to brittle. Thus, in both wx and Wx backgrounds, one dose of Ae-5180 in the endosperm appears to have the same phenotypic effect as 3 doses of the standard ae allele.

An analogous effect can be observed when the Ae-5180 and standard ae alleles are crossed into a homozygous su1 background. It has been reported (Kramer, H. H., Whistler, R. L. and Anderson, E. G., 1956, A new gene interaction in the endosperm of maize. Agronomy Journal 48:170-172) that ae and su1 have an interaction such that kernels homozygous for both mutants are plump, but highly translucent. This unique phenotype is different from that of either homozygous su1 (wrinkled-sugary) or homozygous ae (slightly translucent, slightly wrinkled). We have produced plants that are homozygous su1, but heterozygous for Ae5180, and outcrossed them to homozygous su1 testers. The resulting ears segregate 1:1 for wrinkled-sugary kernels (Ae Ae Ae su1 su1 su1) and plump, translucent kernels (Ae-5180 Ae Ae su1 su1 su1). Thus, in a homozygous su1 background, one dose of Ae-5180 in the endosperm seems to have the same phenotypic effect as 3 doses of the standard ae allele. It should be noted that the phenotypic interactions described for Ae-5180 with wx and su1 are based on the physical appearance of the kernels, and have not been studied yet biochemically.

In a homozygous wx background, pollen that carries the ae allele can be readily distinguished from pollen that carries the wildtype Ae allele by a differential iodine staining technique (Moore, C. W. and Creech, R. G., 1972. Genetic fine structure analysis of the *amylose-extender* locus in *Zea mays* L. *Genetics* 70:611-619). This technique relies on overstaining the pollen grains with iodine, which is taken up by amylose but not amylopectin, followed by heat destaining. The Ae wx pollen grains, which contain amylopectin but no amylose, stain red. The ae wx pollen grains, which contain starch that has at least some characteristics of amylose, stain dark blue. Using this technique, we found that pollen from Ae-5180 Ae wx wx plants had both dark blue and red staining pollen grains in a 1:1 ratio Thus it seems that Ae-5180 wx pollen also stains dark blue, opening up opportunities to use differential staining to study reversion rates of Ae-5180 and to do fine-structure mapping of Ae-5180 with respect to other ae alleles.

As mentioned previously, Ae-5180 frequently shows a reduced frequency of male transmission in competition with the wildtype Ae allele. In order to study this phenomenon further, we utilized several generations of reciprocal outcrosses of heterozygous Ae-5180 Ae plants to standard starchy lines (Ae Ae). All reciprocal crosses were made during the summer of 1987. For the purposes of this discussion, the term "sugary" will be used to describe kernels showing the Ae-5180 phenotype. In all generations, Ae-5180 was fully female transmissible (Tables 5, 6, and 7). However, male transmission varied from generation to generation, and among sibling plants The data in Table 5 present kernel counts from female and male outcross ears of reciprocally crossed plants grown from sugary kernels of the first generation male outcross ear. None of the male outcross ears showed a transmission of Ae-5180 as low as that of the original outcross ear presented in Table 1 (32.4% mutant kernels), and several ears showed normal transmission.

TABLE 5

Counts of starchy (Ae) and sugary (Ae-5180) kernels on exact reciprocal crosses to standard of plants grown from sugary kernels of the first generation male outcross of Ae-5180 to standard.

| | Female Outcross Ears | | | Male Outcross Ears | | |
|---|---|---|---|---|---|---|
| Plant No. | Starchy | Sugary | % Su | Starchy | Sugary | % Su |
| 6093-2 | 161 | 180 | 52.8 | 213 | 171 | 44.5* |
| -3 | 256 | 264 | 50.8 | 345 | 225 | 39.5*** |
| -5 | 195 | 165 | 45.8 | 235 | 170 | 42.0** |
| -7 | 216 | 216 | 50.0 | 259 | 200 | 43.6** |
| -8 | 204 | 186 | 47.7 | 176 | 194 | 52.4 |
| 6094-2 | 221 | 263 | 54.3 | 226 | 144 | 38.9*** |
| -4 | 207 | 245 | 54.2 | 216 | 190 | 46.8 |
| -6 | 272 | 259 | 48.8 | 202 | 191 | 48.6 |
| -9 | 237 | 243 | 50.6 | 312 | 220 | 41.4*** |
| -10 | 214 | 210 | 49.5 | 216 | 215 | 49.9 |
| TOTALS | 2183 | 2231 | 50.5 | 2400 | 1920 | 44.4*** |
| | Homogeneity Chi-square = 11.26 | | | Homogeneity Chi-square = 31.87 | | |

TABLE 5-continued

Counts of starchy (Ae) and sugary (Ae-5180) kernels on exact reciprocal crosses to standard of plants grown from sugary kernels of the first generation male outcross of Ae-5180 to standard.

| Plant No. | Female Outcross Ears | | | Male Outcross Ears | | |
|---|---|---|---|---|---|---|
| | Starchy | Sugary | % Su | Starchy | Sugary | % Su |
| | (df = 9, N.S.) | | | (df = 9, p<0.001) | | |

Symbols:
*chi-square for 1:1 significant at p<0.05
**chi-square for 1:1 significant at p<0.01
***chi-square for 1:1 significant at p<0.001

TABLE 6

Counts of kernels on exact reciprocal crosses to standard of plants grown from sugary kernels of second generation male outcrosses of Ae-5180 to standard.

| Plant No. | Female Outcross Ears | | | Male Outcross Ears | | |
|---|---|---|---|---|---|---|
| | Starchy | Sugary | % Su | Starchy | Sugary | % Su |
| 6097-2 | 308 | 301 | 49.4 | 241 | 207 | 46.2 |
| -7 | 214 | 214 | 50.0 | 231 | 214 | 48.1 |
| -8 | 202 | 161 | 44.4* | 246 | 236 | 48.9 |
| -9 | 250 | 273 | 52.2 | 212 | 287 | 46.9 |
| -11 | 281 | 274 | 49.4 | 300 | 282 | 48.5 |
| 6098-1 | 248 | 287 | 53.6 | 206 | 196 | 48.8 |
| -3 | 207 | 248 | 54.5 | 288 | 265 | 47.9 |
| -4 | 213 | 226 | 51.5 | 264 | 216 | 45.0* |
| -5 | 284 | 277 | 49.4 | 333 | 247 | 42.6*** |
| -8 | 297 | 313 | 51.3 | 229 | 190 | 45.3 |
| TOTALS | 2504 | 2574 | 50.7 | 2550 | 2239 | 46.8*** |
| | Homogeneity | | | Homogeneity | | |
| | Chi-square = 12.28 | | | Chi-square = 7.83 | | |
| | (df = 9, N.S.) | | | (df = 9, N.S.) | | |

Symbols: See Table 5

TABLE 7

Counts of kernels on exact reciprocal crosses to standard of plants grown from sugary kernels of third generation male outcrosses of Ae-5180 to standard.

| Plant No. | Female Outcross Ears | | | Male Outcross Ears | | |
|---|---|---|---|---|---|---|
| | Starchy | Sugary | % Su | Starchy | Sugary | % Su |
| 6101-3 | 138 | 116 | 45.7 | 380 | 289 | 43.2*** |
| -4 | 185 | 187 | 50.3 | 368 | 290 | 44.1** |
| -5 | 159 | 173 | 52.1 | 352 | 226 | 39.1*** |
| -6 | 144 | 140 | 49.3 | 264 | 238 | 47.4 |
| -11 | 201 | 196 | 49.4 | 184 | 144 | 43.9* |
| 6102-2 | 229 | 220 | 49.0 | 302 | 186 | 38.1*** |
| -5 | 167 | 179 | 51.7 | 200 | 178 | 47.1 |
| -9 | 172 | 212 | 55.2* | 401 | 192 | 32.4*** |
| -10 | 272 | 291 | 51.7 | 381 | 291 | 43.3*** |
| -11 | 218 | 215 | 49.7 | 257 | 237 | 48.0 |
| TOTALS | 1885 | 1929 | 50.6 | 3089 | 2271 | 42.4*** |
| | Homogeneity | | | Homogeneity | | |
| | Chi-square = 7.58 | | | Chi-square = 46.95 | | |
| | (df = 9, N.S.) | | | (df = 9, p<0.001) | | |

Symbols: See Table 5.

Table 6 presents kernel counts from reciprocal crosses to standard of plants grown from sugary kernels of second generation male outcross ears. The kernels which were planted to produce family 6097 came from an ear which had 30.8% sugary kernels, and the kernels planted to produce family 6098 came from an ear that had 29.1% sugary kernels. Thus, we expected the plants in families 6097 and 6098 to inherit the system responsible for low male transmission of Ae-5180. As can be seen from the data presented in Table 6, only 2 of 10 plants showed significantly reduced male transmission of Ae-5180.

Table 7 presents kernel counts from reciprocal crosses to standard of plants grown from sugary kernels of third generation male outcross ears. The kernels planted to produce family 6101 came from an ear with 45.6% sugary kernels. The kernels planted to produce family 6102 came from an ear with 45.8% sugary kernels. Most of the male outcross ears of families 6101 and 6102 showed reduced transmission of Ae-5180, with percentages of sugary kernels comparable to those reported in Table 5. There seems to be no pattern to the reduction in male transmission of Ae-5180 other than that it recurs even after several generations of outcrossing. Some workers (Jenkins, and others) have noted transmission anomalies associated with the standard ae allele. Perhaps there is some inherent biochemical effect of mutant *amylose-extender* alleles on the ability of mutant pollen to compete with wildtype Ae pollen. The degree to which the competition of mutant pollen is affected might be influenced by genetic background and/or environment. This would not be without precedent, since wx pollen grains have been observed to germinate more slowly than Wx pollen grains in certain genetic backgrounds, resulting in a lowered frequency of wx transmission. The standard starchy lines that we use in our outcross studies have as their genetic background four different inbred lines. Thus, the individual plants in our male transmission studies are fairly heterogeneous. This could account for the wide variation in male transmission that we observe. As mentioned previously, we are in the process of moving Ae-5180 into several different inbred backgrounds in order to control genetic variation in these experiments.

In order to be certain that the reduced male transmission observed in our experiments is a real effect, and not due to poor penetrance of Ae-5180 in some of the heterozygous kernels in the male outcrosses, 100 phenotypically starchy kernels from second-generation male outcross ears were planted, and the resulting plants selfed. Out of 76 ears obtained, none segregated for sugary kernels. Therefore, the reduced number of sugary kernels in male outcross ears is due to a real reduction in male transmission of Ae-5180, and not due to poor expression of the gene. Note: Because this effect has its basis in competition and is not due to some variability in the expression of the Ae-5180 allele, it will not affect the usefulness of this unique mutant.

Summarizing, in all respects, Ae-5180 behaves as a dominant mutant allele of *amylose-extender*.

PRACTICE OF INVENTION

The transposable element-induced, dominant ae allele Ae-5180, described above, has been transferred to a larger population of hybrid seeds: A collection of the seeds (25 packets with 25 seeds per packet) of Code No. Ae-5180/stand B70 has been deposited with the American Type Culture Collection, Rockville, Maryland. Viability of the deposited seeds was confirmed, and the seeds were assigned ATCC Accession No. 40499. These seeds all carry a single transferrable copy of the dominant mutant allele of *amylose*-i extender, Ae-5180. By using plants grown from these kernels in crosses, Ae-5180 can be transferred into any maize genetic background desired.

The present invention extends to methods for producing inbred and hybrid maize seeds with the dominant *amylose-extender* allele, Ae-5180 corresponding to the Ae-5180 mutant or the ATCC deposited seeds (Accession No. 40499). Such seeds can be used for growing high-amylose starch maize and for producing high-amylose maize seeds in bulk.

Inbred Ae-5180 Line Production: The production of inbred Ae-5180 lines will be accomplished by crossing an Ae-5180 stock to the selected inbreds and repeatedly backcrossing to the inbred lines for 6 or 7 (or more) generations. Kernels carrying Ae-5180 should be selected for planting each generation. After the last backcross, kernels carrying Ae-5180 should be planted and the resulting plants self-pollinated. Ae-5180 kernels selected from the self-pollinated ears should be sown and the resulting plants self-pollinated. One third of the resulting ears will be homozygous for the Ae-5180 allele and thus would be the desired Ae-5180 conversion inbred line.

Hybrid Ae-5180 Line Production: Once Ae-5180 versions of inbred lines are produced, standard breeding methods for generating hybrid seed can be utilized. (Note: Due to the fact that Ae-5180 is a dominant, the reduction in yield of high amylose kernels that results from contamination from field corn in the present day high amylose production field utilizing the recessive ae alleles, will not occur.)

A unique production method for high amylose seeds using Ae-5180: Because Ae-5180 is dominant and is responsible for amylose levels of 70% in one or two doses in the endosperm, it will be possible to use Ae-5180 inbred or hybrid lines as male parents and high yielding (elite) Ae Ae hybrids as female parents in a production field in which the hybrid parents are either male sterile or detasseled. Although this production method is more expensive than the previous production method using hybrid Ae-5180 lines, the potential elevated yield of high amylose seeds may more than offset these additional costs. Both male and female parents can serve as a source of high amylose seeds.

We claim:

1. High amylose starch maize seeds containing at the *amylose-extender* (ae) locus at least one dominant mutant allele Ae-5180.

2. High amylose maize seeds produced by crossing two maize lines, said seeds containing at the *amylose-extender* (ae) locus at least one dominant mutant allele Ae-5180.

3. High amylose starch maize seeds containing at the *amylose-extender* (ae) locus homozygous Ae-5180 alleles.

4. The maize seeds of claim 3 which are hybrid maize seeds.

5. The maize seeds of claim 3 which are inbred maize seeds.

6. Maize plants grown from the maize seeds of claims 1, 2, 3, 4, or 5.

7. Viable maize seeds and plants and succeeding generations thereof grown from the seeds deposited under ATCC Accession No. 40499, and maize seeds and plants to which the Ae-5180 dominant mutant allele is transferred from said deposited seeds or succeeding generations thereof.

8. The method of developing hybrid maize seeds containing high amylose starch, comprising crossing a first maize line with a second maize line, at least one of said lines containing at its *amylose-extender* (ae) locus at least one dominant mutant allele Ae-5180.

9. The method of claim 8 in which at least one of said lines contains at the *amylose-extender* (ae) locus homozygous Ae-5180 alleles.

10. The method of claim 8 in which both of said lines contain at the *amylose-extender* (ae) locus homozygous Ae-5180 alleles.

11. The method for directly producing high amylose maize seeds, comprising crossing a homozygous Ae-5180 line as a male onto a detasseled or male sterile wild type (Ae Ae) hybrid maize line.

* * * * *

UNITED STATES PATENT AND TRADEMARK OFFICE
CERTIFICATE OF CORRECTION

PATENT NO. : 5,004,864

DATED : April 2, 1991

INVENTOR(S) : Robertson et al.

It is certified that error appears in the above-identified patent and that said Letters Patent is hereby corrected as shown below:

Column 1, in lines 27, 31 and 57, delete "E.F." and substitute --Whistler, BeMiller, and--.

Column 1, lines 47, cancel "processing" and substitute --possessing--.

Column 2, line 20, cancel "perdent" and substitute --percent--.

Column 6, line 40, after "plants" insert a period.

Column 8, line 55, cancel "stand" and substitute --Stand--.

Column 8, line 60, cancel "amylose-i extender" and substitute --amylose-extender--.

Signed and Sealed this

Second Day of March, 1993

Attest:

STEPHEN G. KUNIN

*Attesting Officer*   *Acting Commissioner of Patents and Trademarks*